(12) United States Patent
Fan et al.

(10) Patent No.: US 10,829,814 B2
(45) Date of Patent: Nov. 10, 2020

(54) METHODS AND COMPOSITIONS FOR SINGLE CELL GENOMICS

(71) Applicants: Illumina, Inc., San Diego, CA (US); The Regents of the University of California, Oakland, CA (US)

(72) Inventors: Jian-Bing Fan, San Diego, CA (US); Kun Zhang, San Diego, CA (US)

(73) Assignees: Illumina, Inc., San Diego, CA (US); The Regents of the University of Caliofrnia, Oakland, CA (US)

( * ) Notice: Subject to any disclaimer, the term of this patent is extended or adjusted under 35 U.S.C. 154(b) by 508 days.

(21) Appl. No.: 14/742,027

(22) Filed: Jun. 17, 2015

(65) Prior Publication Data

US 2015/0368704 A1    Dec. 24, 2015

Related U.S. Application Data

(60) Provisional application No. 62/014,538, filed on Jun. 19, 2014.

(51) Int. Cl.
*C12P 19/34*   (2006.01)
*C12Q 1/6874*  (2018.01)
*C12Q 1/6841*  (2018.01)

(52) U.S. Cl.
CPC ......... *C12Q 1/6874* (2013.01); *C12Q 1/6841* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3, 25.32
See application file for complete search history.

(56) References Cited

U.S. PATENT DOCUMENTS

| | | | | |
|---|---|---|---|---|
| 6,074,868 A | * | 6/2000 | Blumenfeld | B01L 7/52 435/286.1 |
| 2008/0113358 A1 | * | 5/2008 | Kapur | G01N 33/689 435/6.12 |
| 2015/0105298 A1 | * | 4/2015 | Czaplinski | C12Q 1/682 506/16 |

OTHER PUBLICATIONS

Nuovo, In situ PCR: protocols and applications. Genome Res., 4, S151-S167, 1995.*
Ebina et al., In situ detection of unexpected patterns of mutant p53 gene expression in non-small cell lung cancers. Oncogene, 20, 2579-2586, 2001.*
Gunderson et al., "Decoding Randomly Ordered DNA Arrays," Genome Research, vol. 14, pp. 870-877, 2004.

* cited by examiner

*Primary Examiner* — Frank W Lu
(74) *Attorney, Agent, or Firm* — Gavrilovich, Dodd & Lindsey LLP

(57) ABSTRACT

Presented are methods and compositions for obtaining sequence information from one or more individual cells. The methods are useful for obtaining sequence information for a single nucleotide sequence, and for multiplex generation of sequence information from one or more individual cells.

8 Claims, 1 Drawing Sheet

Specification includes a Sequence Listing.

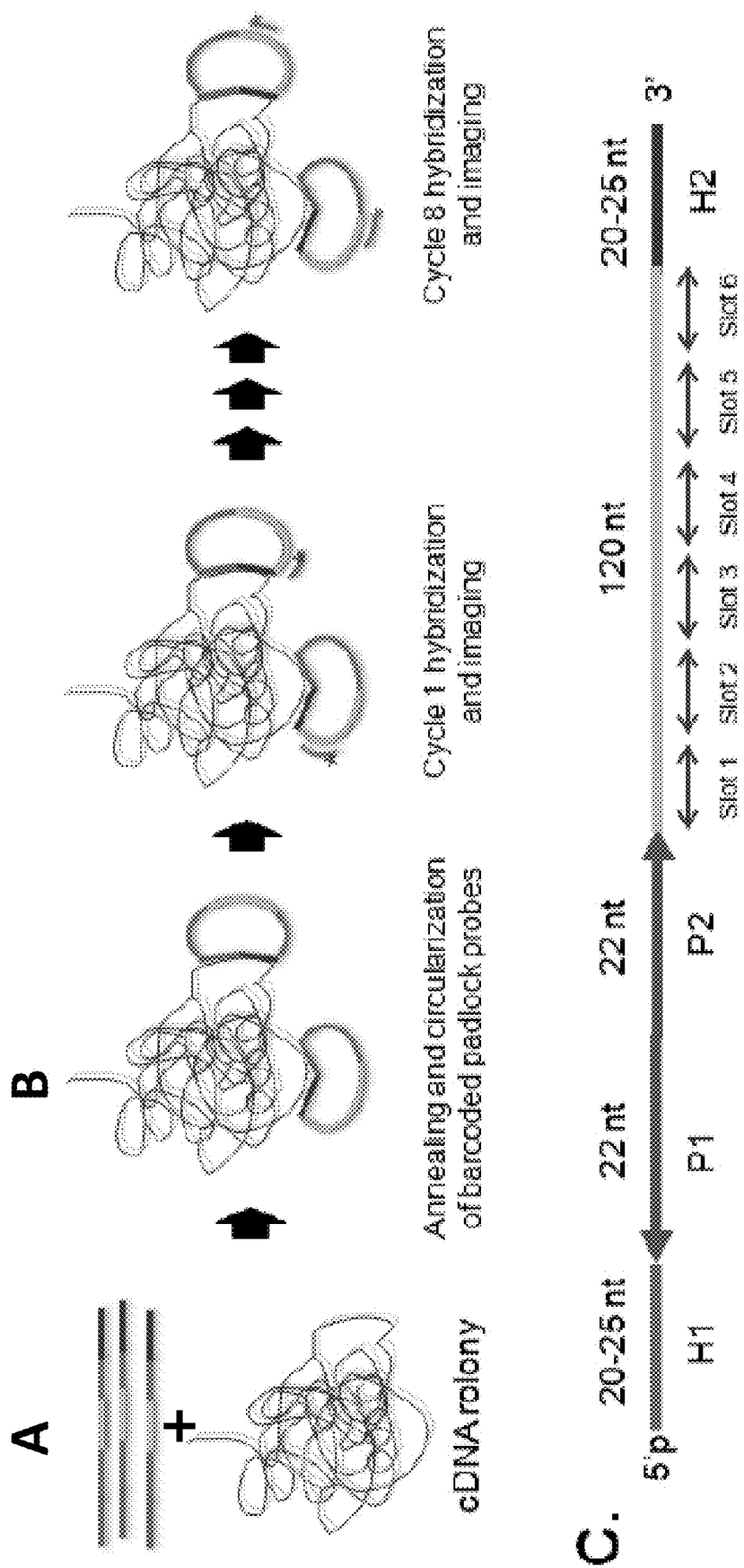

SEQUENCE LISTING

<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aactgatggg acccactcca tcg                                         23

<210> SEQ ID NO 2
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 2
wctgtagcta gaccaaaatc accta                                           25

<210> SEQ ID NO 3
<211> LENGTH: 92
<212> TYPE: DNA
<213> ORGANISM: Homo sapiens

<400> SEQUENCE: 3
ccagacaact gttcaaactg atgggaccca ctccatcgag atttcwctgt agctagacca     60
aaatcaccta tttttactgt gaggtcttca tg                                   92

<210> SEQ ID NO 4
<211> LENGTH: 126
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cgatggagtg ggtcccatca gttatgtatc gcgctcgatt ggcagtagaa cttgcgcgga     60
tacacggtcg aggtccgact cggaatacgt cgttgactgc gtaggtgatt ttggtctagc   120
tacagt                                                               126

<210> SEQ ID NO 5
<211> LENGTH: 126
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cgatggagtg ggtcccatca gttacgtatc ggtagtcgca acgcatctac ttcgtcgcgt     60
cagaccatcg aggtccgacc taccattcgc gtgcgattcc ataggtgatt ttggtctagc   120
tacaga                                                               126

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccaccgtgca gctcatcay                                                  19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
catgcccttc ggctgcctcc t                                               21

<210> SEQ ID NO 8
<211> LENGTH: 92
<212> TYPE: DNA
<213> ORGANISM: Homo sapiens

<400> SEQUENCE: 8
tgccgcctgc tgggcatctg cctcacctcc accgtgcagc tcatcaygca gctcatgccc    60
ttcggctgcc tcctggacta tgtccgggaa ca    92

<210> SEQ ID NO 9
<211> LENGTH: 118
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
catgcccttc ggctgcctcc tgtcttgcgt gcgatacgga gtacgaattg tccgcgctct    60
acgattcgag gtccgactcg gaatacgtcg ttgactgcgc caccgtgcag ctcatcac    118

<210> SEQ ID NO 10
<211> LENGTH: 118
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
catgcccttc ggctgcctcc tcaacggtat tcggtcgtca tccccgtttg atcgttcgac    60
cgagatcgag gtccgaccta ccattcgcgt gcgattccac caccgtgcag ctcatcat    118

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcaagatca cagattttgg gck    23

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctgctgggtg cggaagagaa agaata    26

<210> SEQ ID NO 13
<211> LENGTH: 92
<212> TYPE: DNA
<213> ORGANISM: Homo sapiens

<400> SEQUENCE: 13
gtactggtga aaacaccgca gcatgtcaag atcacagatt ttgggckggc caaactgctg    60
ggtgcggaag agaaagaata ccatgcagaa gg    92

<210> SEQ ID NO 14
<211> LENGTH: 127
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ctgctgggtg cggaagagaa agaatataga acttgcgcgg atacacggcg aattgtccgc      60
gctctacgat tcgaggtccg acctaccatt cgcgtgcgat tccagtcaag atcacagatt     120
ttgggct                                                               127

<210> SEQ ID NO 15
<211> LENGTH: 127
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctgctgggtg cggaagagaa agaatacaac ggtattcggt cgtcatcctc tacttcgtcg      60
cgtcagacca tcgaggtccg actcggaata cgtcgttgac tgcggtcaag atcacagatt     120
ttgggcg                                                               127

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agctctttga ggacaactat gcgctg                                           26

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agacaatgga gacccgctga ac                                               22

<210> SEQ ID NO 18
<211> LENGTH: 100
<212> TYPE: DNA
<213> ORGANISM: Homo sapiens

<400> SEQUENCE: 18
tgtgcgaggc acccagctct ttgaggacaa ctatgccctg gccgtgctag acaatggaga      60
cccgctgaac aataccaccc ctgtcacagg ggcctcccca                           100

<210> SEQ ID NO 19
<211> LENGTH: 126
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 19
agacaatgga gacccgctga acacgtatcg gtagtcgcaa cgcaccgttt gatcgttcga    60
ccgagatcga ggtccgacct accattcgcg tgcgattcca agctctttga ggacaactat   120
gcgctg                                                              126

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cctgctctct ctgtctcaac                                                20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgctgccca ggacttcttg cc                                             22

<210> SEQ ID NO 22
<211> LENGTH: 119
<212> TYPE: DNA
<213> ORGANISM: Homo sapiens

<400> SEQUENCE: 22
ctactggggc ccacttcctc tcctgctctc tctgtctcaa cgtgattgac tttcttgtgc    60
tgcccaggac ttcttgccca cgtgcgcctt caaaacggta agagctgcaa ctgaacgtg    119

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atgtatcgcg ctcgattggc agtagaactt gcgcggatac acgg                     44

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gtgctgccca ggacttcttg ccatgtatcg cgctcgattg gcaggtcttg cgtgcgatac    60
ggagtatcga ggtccgaccg aattgtccgc gctctacgat cctgctctct ctgtctcaac   120

METHODS AND COMPOSITIONS FOR SINGLE CELL GENOMICS

STATEMENT REGARDING FEDERALLY SPONSORED RESEARCH

This invention was made with Government support under grant number MH098977 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 23, 2015, is named IP-0645-US_SL.txt and is 6,791 bytes in size.

BACKGROUND

Historically, many biological questions were addressed by gene expression analysis of many cells. One of the shortcomings of this strategy is that gene expression heterogeneity, which is present even among genetically identical cells that are grown in the same culture or are found at the same developmental point, is obscured. As a result, the gene expression profile of individual cells and the cell-to-cell variability will be lost, as they become part of the average, and single cell level analyses are required to provide information about these aspects.

A general strategy in existing single-cell transcriptome analysis methods is to amplify the limited number of RNA molecules from a cell and quantify the transcript abundance by hybridization or sequencing. A key challenge is that all RNA species in the target cells need to be amplified specifically and uniformly to a large quantity with little loss. There remains a great need for robust methods that are inherently scalable and automatable, and that, most importantly, can provide accurate quantitative information of all RNA species regardless of the length and presence or absence of 3' poly-A tails.

Another layer of information in single cell expression analysis is the three dimensional map of transcriptional activities in single cells. In the past, after being isolated, tissue samples were trypsinized and the resulting cell suspensions were used to examine individual cells, but during this procedure, the spatial relationship among cells from the original tissue sample was lost. Mapping the specific individual cells back to the three-dimensional organ or tissue is challenging, but this is the future direction which single cell gene expression profiling will develop. It is fundamental for understanding cellular functions that shape development and disease.

BRIEF SUMMARY

Presented herein are methods and compositions for obtaining sequence information from one or more individual cells. The methods are useful for obtaining sequence information for a single nucleotide sequence, and for multiplex generation of sequence information from an individual cell. In some embodiments presented herein, the methods comprise first amplifying one or more nucleic acid molecules in situ within a cell, and subsequently hybridizing a barcode probe to the amplified nucleic acid molecules. The identity of the amplified nucleic acid molecules is then determined by decoding of the barcode probes. In other embodiments presented herein, the methods comprise first hybridizing one or more different barcode probes to one or more nucleic acid molecule in situ within a cell, and subsequently amplifying the barcode probe, thereby generating an amplified barcode probe. The identity of the nucleic acid molecules is then determined by decoding of the amplified barcode probes.

Accordingly, presented herein is a method of obtaining sequence information from an individual cell comprising: amplifying a nucleic acid molecule in situ within a cell, thereby generating an amplified nucleic acid molecule; annealing in situ a barcode probe comprising at least a first decoder sequence and a second decoder sequence to the amplified nucleic acid molecule; hybridizing a first labeled decoder probe to the first decoder sequence; detecting a signal indicative of the hybridizing; hybridizing a second labeled decoder probe to the second decoder sequence; and detecting a signal indicative of the hybridizing, thereby generating sequence information regarding the amplified nucleic acid molecule.

Also presented herein is a method of obtaining sequence information regarding a plurality of nucleic acid molecules from an individual cell comprising: amplifying a plurality of nucleic acid molecules in situ within a cell, thereby generating a set of amplified nucleic acid molecules; for each of a plurality of amplified nucleic acid molecules in the set, annealing in situ a barcode probe comprising at least a first decoder sequence and a second decoder sequence to the amplified nucleic acid molecule; and hybridizing a first labeled decoder probe to the first decoder sequence; detecting a plurality of signals indicative of the hybridizing; hybridizing a second labeled decoder probe to the second decoder sequence; and detecting a plurality of signals indicative of the hybridizing, thereby generating sequence information regarding the plurality of amplified nucleic acid molecules.

Also presented herein is a method of obtaining sequence information from an individual cell comprising: annealing a barcode probe specific for a disease-causing mutation to a nucleic acid molecule in situ within a cell, the barcode probe comprising at least a first decoder sequence and a second decoder sequence; amplifying the barcode probe in situ, thereby generating an amplified barcode probe; hybridizing a first labeled decoder probe to the first decoder sequence; detecting a signal indicative of the hybridizing; hybridizing a second labeled decoder probe to the second decoder sequence; and detecting a signal indicative of the hybridizing, thereby generating sequence information regarding the amplified nucleic acid molecule.

Also presented herein is a method of obtaining sequence information from a plurality of individual cells in parallel. The cells can be a pool of cell populations from blood or any liquid biospecimen. The cells can also be many cells from a tissue section in which the original spatial relationships of the cells are retained.

In some aspects of the above embodiments, the first labeled decoder probe is removed prior to hybridizing the second labeled decoder probe. In some aspects, the second labeled decoder probe is hybridized prior to the first labeled decoder probe.

In certain aspects, detecting can comprise sequencing at least the first decoder sequence in situ. Detecting can also further comprise sequencing at least the second decoder sequence in situ.

In certain aspects, amplifying comprises rolling circle amplification. In certain aspects, the barcode probe can comprise a rolling circle amplification probe, such as a padlock probe. In certain aspects, the barcode probe comprises an oligonucleotide ligation assay probe.

In certain aspects, the amplified nucleic acid molecule or molecules are immobilized within the one or more cells.

In certain aspects, the amplified nucleic acid molecule is amplified from an RNA template, for example by cDNA synthesis using the RNA as a template. In certain aspects, the amplified nucleic acid molecule comprises DNA.

In certain aspects, the nucleic acid molecule comprises a disease-causing mutation, allele or common variant. In certain such aspects, the methods can comprise hybridizing a barcode probe which is correlated with the disease-causing mutation, allele or common variant. In some aspects, the method can comprise ligation of a mutation-specific padlock probe only when the disease-causing mutation, allele or common variant is present in the nucleic acid molecule. The disease-causing mutation, allele or common variant can be, for example, a base substitution, an insertion mutation, a deletion mutation, a gene amplification, a gene deletion, a gene fusion event, a gene inversion invent and the like.

In some aspects, detecting can further comprise evaluating a signal to determine the presence, quantity, frequency, and/or spatial distribution of a disease-causing mutation, allele or common variant within a tissue.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 describes one embodiment of padlock capture and hybridization decoding of rolonies. (A) Molecular barcodes are attached to rolonies in a gene specific manner using padlock probes. (B) After padlock capture, each rolony will have a unique barcode in thousands of copies. These barcodes can be accurately decoded by hybridization similar to the decoding of Illumina bead array, using a combinatorial chemistry approach (Gunderson et al. Genome Res. 14(5): 870-877 (2004)). (C) Schematic of padlock probes. In the example shown, each probe has two gene-specific (and/or allele-specific) capturing arms H1/H2. The region in the middle contains six slots for hybridization barcodes. In an alternative embodiment, the padlock probe can be replaced with two independent probes, for example, two oligo ligation probes—one contains the barcode sequences and upstream target-specific sequence and one contains downstream target-specific sequences (and with or without barcode sequences).

DETAILED DESCRIPTION

Existing whole transcriptome amplification methods involve lengthy processing with a large number of experimental steps which do not allow for automation and implementation at a production scale. Thus, there remains a great need for a robust method that is inherently scalable and automatable, and that, importantly, can provide accurate quantitative information of all RNA species regardless of the length and presence or absence of 3' poly-A tails.

Spatial information is also desirable when interpreting transcriptional heterogeneity of individual cells in a structured tissue. However, RNA sequencing is typically performed on isolated cells, such that spatial information is lost. One existing approach to link transcriptome information from isolated cells to their context is to first acquire the spatial information as well as other "phenotypes" of individual cells within the intact tissue using fluorescent microscopy, and then extract specific cells (or cellular content) for subsequent transcriptional profiling. Thus, there is a need for methods which provide high-resolution mapping of a large number of transcripts in situ.

Accordingly, presented herein are methods and compositions for obtaining sequence information from an individual cell. The methods are useful for obtaining sequence information at the level of individual nucleic acid molecules. The methods are especially advantageous for multiplex generation of sequence information from an individual cell. As such, sequence information can be obtained for several individual nucleic acid molecules in an individual cell. In some embodiments presented herein, the methods comprise first amplifying one or more nucleic acid molecules in situ within a cell, and subsequently hybridizing a barcode probe to the amplified nucleic acid molecules. The identity of the amplified nucleic acid molecules is then determined by decoding of the barcode probes. In other embodiments presented herein, the methods comprise first hybridizing one or more different barcode probes to one or more nucleic acid molecule in situ within a cell, and subsequently amplifying the barcode probe, thereby generating an amplified barcode probe. The identity of the nucleic acid molecules is then determined by decoding of the amplified barcode probes.

The methods and compositions set forth herein will be exemplified for detection of nucleic acids in a single cell. However, the methods can be extended to the simultaneous detection of nucleic acids in several individual cells. Parallel detection can be carried out such that several individual cells are resolved with regard to nucleic acid sequences that are present. In some embodiments the spatial location of nucleic acids can be simultaneously determined for several individual cells in a tissue or other cell-containing sample. It will be understood that particular embodiments of the methods set forth herein have broader use and need not be used to resolve individual cells. Rather the methods can be used to detect nucleic acids in a collection of several cells where the cells are not individually resolved with respect to which of the cells do or do not contain a particular sequence present in the collection of cells.

Barcode Probes for Detection of Amplified Nucleic Acid Molecules

The methods and compositions presented herein relate to obtaining sequence information from an individual cell. In some embodiments of the methods provided herein, the methods comprise first amplifying one or more nucleic acid molecules in situ within a cell, and subsequently hybridizing a barcode probe to the amplified nucleic acid molecules. The identity of the amplified nucleic acid molecules is then determined by decoding of the barcode probes.

Thus, in certain embodiments, the methods can comprise amplifying a nucleic acid molecule in situ within a cell, thereby generating an amplified nucleic acid molecule. As used herein, the term in situ refers to analysis methods which are performed within a cell or tissue. In some embodiments, an in situ analysis method is performed in a viable cell which is capable of performing one or more cellular functions typically associated with a living cell, such as respiration, cellular transport, transcription, translation and the like. In some embodiments, an in situ analysis method is performed in a cell that is not viable, but retains the structure and organization of a viable cell. For example, a cell which has been permeabilized and/or fixed is not considered viable, even though subcellular organelles and molecules such as proteins and nucleic acids remain intact and substantially in the same cellular location compared to a viable cell. Thus, analysis methods such as amplification, annealing, hybridizing, decoding and the like which are performed in situ are performed within the structure of a viable or non-viable cell or tissue. In some embodiments, the individual cell has been isolated from its original tissue, for example, using laser capture microdissection or any other suitable isolation technique as known in the art. In other embodiments, the individual cell remains within the context of its original surrounding tissue. For example, the individual cell can be part of a tissue slice from frozen or paraffin-embedded tissue. Thus, in some embodiments, the methods presented herein can be performed on a plurality of individual cells simultaneously.

Barcode Probes

The methods provided herein further comprise annealing in situ a barcode probe to the amplified nucleic acid molecule. As used herein, the term barcode probe refers to a nucleic acid molecule which can hybridize specifically to a nucleic acid of interest, and which comprises a barcode sequence. As used herein, the terms barcode, barcode sequence and like terms refer to a unique identifier sequence on a probe molecule. The unique identifier sequence can be, for example, a nucleic acid sequence which associates the barcode probe with the nucleic acid of interest to which it hybridizes.

The barcode probes presented herein can be any probe which specifically hybridizes to a nucleic acid species of interest and which comprises at least a first and a second decoder sequence. In some embodiments presented herein, the barcode probes are used as a template for further amplification, thus generating a clonal object that comprises many repeating copies of the barcode, as described in greater detail in the disclosure of WO 2011/123246, the entire content of which is incorporated herein by reference in its entirety. As used herein, the terms "clonal object" refers to a particle having a nucleic acid sequence in one or more copies. An exemplary clonal object is a nucleic acid that has been amplified from a target nucleic acid molecule and in some aspects has a single tandemly repeated sequence of the target nucleic acid molecule. Such tandemly repeated sequences may also be separated with non-target nucleic acids, such as primer binding sites, endonuclease recognition sites, nucleotides linked to affinity ligands or the like. In particular embodiments a clonal object can be a DNA ball, for example, formed by rolling circle amplification. Methods of generating a clonal object are well known to one of skill in the art and exemplary methods are also described herein. As used herein, a "clonal object" can be synthesized using an amplification technique and thus is a type of amplicon. Accordingly, an amplicon is the nucleic acid product of an amplification reaction.

A method for generating an array of amplified nucleic acid sequences can include the step of attaching at least one second universal primer having a second common priming site to a plurality of sample nucleic acid molecules, thereby attaching a first universal primer and a second universal primer to a sample nucleic acid molecule of the plurality of sample nucleic acid molecules. In a particular embodiment, the first universal primer and the second universal primer can be attached to respective ends of each nucleic acid in the plurality of sample nucleic acid molecules by ligation.

In embodiments that include ligation of a first double stranded nucleic acid end to a second double stranded nucleic acid end, the ends to be ligated can be blunt or can have complementary single stranded overhangs. The use of complementary overhangs generally provides an added measure of specificity over blunt end methods because conditions can be used in which non-complementary sequences will not ligate. Further specificity can be attained by partially filling in one overhang end to make it complementary to another end. This fill in method can be used to disfavor unwanted ligation between nucleic acids in a sample that were generated with the same restriction enzyme.

An amplicon typically contains multiple, tandem copies of the circularized nucleic acid molecule of the corresponding sample nucleic acid. That is, each amplicon contains multiple, tandem copies of a single sample nucleic acid molecule, which was circularized. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the particular application. As disclosed herein, one particular form of an amplicon is as a nucleic acid "ball" having desired dimensions. The number of copies of the nucleic acid molecule can therefore provide a desired size of a nucleic acid "ball" or a sufficient number of copies for efficient subsequent analysis of the amplicon, for example, sequencing.

The terms "target nucleic acid," "target nucleic acid molecule," "target nucleic acid species" and any grammatical equivalent thereof, refer to nucleic acid molecules that are desired to be detected, sequenced or otherwise analyzed. Any of a variety of desired target nucleic acid molecules can be utilized, including but not limited to exons, or nucleic acid molecules complementary thereto; cDNA molecules, or nucleic acid molecules complementary thereto; untranslated regions (UTRs) or nucleic acids complementary thereto; promoter and/or enhancer regions, or nucleic acid molecules complementary thereto; evolutionary conserved regions (ECRs), or nucleic acid molecules complementary thereto; transcribed genomic regions, or nucleic acid molecules complementary thereto. Any of a variety of methods can be used to obtain targeted nucleic acid molecules, as disclosed herein. Such methods include, but are not limited to, obtaining a targeted nucleic acid molecule using hybridization-extension capture enrichment; using targeted restriction sites, for example, using an oligonucleotide engineered with a hairpin having a Type IIS restriction enzyme site such as a FokI restriction enzyme site and a locus-specific region; using locus-specific hyperbranched rolling circle amplification; using random-locus-specific primer amplification; using multiplex emulsion PCR; using multiplex bridge PCR; using padlock probe amplification; and using mini-libraries from targeted libraries, as disclosed herein.

As used herein, the terms "target nucleic acid sequence," "sample nucleic acid sequence" and like terms refer to nucleic acid sequences obtained from samples that are desired to be analyzed.

A nucleic acid sample that is amplified, sequenced or otherwise manipulated in a method disclosed herein can be, for example, DNA or RNA. Exemplary DNA species include, but are not limited to, genomic DNA (gDNA), mitochondrial DNA, chloroplast DNA, episomal DNA, viral DNA and copy DNA (cDNA). One non-limiting example of a subset of genomic DNA is one particular chromosome or one region of a particular chromosome. Exemplary RNA species include, without limitation, coding RNA such as messenger RNA (mRNA), and non-coding RNA (ncRNA) such as transfer RNA (tRNA), microRNA (miRNA), small nuclear RNA (snRNA) and ribosomal RNA (rRNA). Further species of DNA or RNA include fragments or portions of the species listed above or amplified products derived from these species, fragments thereof or portions thereof. The methods described herein are applicable to the above species encompassing all or part of the complement present in a cell. For example, using methods described herein the sequence of a substantially complete genome can be determined or the sequence of a substantially complete targeted nucleic acid sequences such as mRNA or cDNA complement of a cell can be determined.

Useful methods for clonal amplification from single molecules include, for example, rolling circle amplification (RCA) (Lizardi et al., *Nat. Genet.* 19:225-232 (1998), which is incorporated herein by reference) and oligonucleotide ligation assay (OLA) (See generally U.S. Pat. Nos. 7,582, 420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. The enhanced signal-to-noise ratio provided by clonal amplification provides a great advantage over existing detection methodologies.

In a particularly useful embodiment, amplicons are generated by rolling circle amplification (RCA), which can be used to generate amplicons having multiple copies of a nucleic acid sequence and which can be used to create nucleic acid "balls," as disclosed herein. It will be understood that these "balls" need not be perfectly spherical and can include other globular or packed conformations. In a particular embodiment, RCA is primed using the at least one universal primer attached to the sample nucleic acid molecule.

Barcode probes used in the methods presented herein can include padlock probes. Padlock probes are specialized ligation probes and are known in the art, as exemplified generally by Nilsson et al, 1994, Science 265:2085, hereby incorporated by reference. These probes have a first ligation domain that is identical to a first ligation probe, in that it hybridizes to a first target sequence domain, and a second ligation domain, identical to the second ligation probe, that hybridizes to an adjacent target sequence domain. Again, as for OLA, the detection position can be either at the 3' end of the first ligation domain or at the 5' end of the second ligation domain. However, the two ligation domains are connected by a linker, frequently nucleic acid. The configuration of the system is such that upon ligation of the first and second ligation domains of the padlock probe, the probe forms a circular probe, and forms a complex with the target sequence wherein the target sequence is "inserted" into the loop of the circle.

Specific padlock probes are useful for the methods provided herein and include, for example, padlock probes for genomic analyses, as exemplified by Gore, A. et al. Nature 471, 63-67 (2011); Porreca, G. J. et al. Nat Methods 4, 931-936 (2007); and Li, J. B. et al. Genome Res 19, 1606-1615 (2009), the content of each of which is incorporated by reference in its entirety.

Other padlock probes useful for the methods provided herein include, for example, padlock probes for transcriptomic analyses, as exemplified by Zhang, K. et al. Nat Methods 6, 613-618 (2009); Noggle, S. et al. Nature 478, 70-75 (2011); and Li, J. B. et al. Science 324, 1210-1213 (2009), the content of each of which is incorporated by reference in its entirety.

Other examples of padlock probes useful for the methods provided herein include, for example, padlock probes for methylomic analyses, as exemplified by Deng, J. et al. Nat Biotechnol 27, 353-360 (2009); Hansen, K. D. et al. Nat Genet 43, 768-775 (2011); Diep, D. et al. Nature Methods (2012), the content of each of which is incorporated by reference in its entirety.

As disclosed herein, the amplicons can be compacted prior to hybridizing or binding to a bead described herein. Methods of compacting amplicons are known in the art (for example, as described by Bloomfield, *Curr. Opin. Struct. Biol.* 6(3): 334-41 (1996), and Drmanac et al., US 2007/0099208 A1, each of which is incorporated herein by reference) and disclosed herein. For example, an alcohol or polyamine such as spermine or spermidine can be used. A compacted nucleic acid will have a structure that is more densely packed than the structure of the nucleic acid in the absence of a compacting agent or compacting condition and the structure will typically resemble a ball or globule. The generation of such compacted nucleic acid balls is useful for fabricating one clonal object bound to one bead, as discussed herein in more detail. Various methods can be used to generate balls of a desired size, for example, using various compacting techniques and/or varying the number of copies in an amplicon. Generally, the compacted amplicons have an average diameter or width ranging from about 0.1 µm to about 5 µm, for example, about 0.1 µm, about 0.2 µm, about 0.5 µm, about 1 µm, 2 µm, about 3 µm, about 4 µm and about 5 µm.

Decoder Sequences and Decoder Probes

The methods and compositions presented herein make use of unique barcode probes having decoder sequences to identify multiple nucleic acid targets in a multiplex fashion. The instant innovations overcome limitations of existing rolony identification methodologies by surprisingly and successfully applying decoding strategies that entail sequential hybridizations of labeled decoder probes to decoder sequences found in immobilized nucleic acids within an individual cell. Such decoding strategies using decoder sequences have until now been used for decoding of randomly assembled arrays of beads. Thus, the decoding strategies presented herein are flexible and scalable and can be used to detect and decode thousands of unique amplified nucleic acid species.

In some embodiments, a barcode probe can comprise at least a first decoder sequence and a second decoder sequence. In some embodiments, a barcode probe can comprise 2, 3, 4, 5, 6, 7, 8, 9, 10 or more than 10 decoder sequences. As used herein, the terms decoder sequence, stage, slot and like terms refer to a unique sequence which is part of a plurality of unique sequences are designed to each specifically hybridize to a labeled decoder probe. During decoding, labeled decoder probe oligonucleotides are sequentially hybridized to the decoder sequences to specifically determine the identity of each barcode sequence. Sequential hybridization of decoder probes to decoder sequences is described by Gunderson et al. (Genome Res. (2004) 14:870-877), the content of which is incorporated by reference in its entirety. Additional description of decoding algorithms and the use of sequential hybridization useful in the methods presented herein can be found in U.S. Pat. Nos. 7,060,431; 7,033,754; 7,226,734; and 7,455,971, the disclosures of each of which are hereby incorporated by reference in their entireties. The principles of sequential hybridization to decode bead arrays are surprisingly robust and effective when applied to amplified nucleic acids in situ according to the methods provided herein.

As an example, one or more target nucleic acid species can be amplified, either specifically or non-specifically, to generate an amplified molecule containing many repeats of the amplified nucleic acid in tandem. In the embodiment shown in FIG. 1, cDNA is generated in situ, using either random hexamers or oligo dT primers or both. Then the cDNA molecules are amplified using rolling circle amplification (RCA) to generate a "DNA ball" or "rolony". The amplified nucleic acids can then be hybridized with one or more unique padlock probes with unique molecular barcodes. When a padlock probe specifically hybridizes to a sequence of interest, the probe is ligated to form, for example, a circularized barcoded padlock probe. The amplified nucleic acid molecules and/or the hybridized padlock probes are immobilized within the cell using the crosslinking methods described herein, and decoding of the barcode probe takes place by multiple rounds of sequential hybridization. In the example shown in FIG. 1, decoding takes place via a set of barcode probes having decoder sequences that can be decoded by eight rounds of sequential hybridization with fluorescently labeled oligos and imaging of fluorescent images.

The decoding strategies presented herein provide several key advantages over existing sequence identification methods. For example, one advantage is the simplicity and robustness of the decoding process, which involves hybridization and washing of oligo pools at room temperature. As such, heating and cooling steps are not necessary, thus minimizing damage to the cellular structure and reducing the potential drift of the specimen throughout the imaging process. As an additional advantage, the signals that are generated are more even and have higher intensity inside a structured tissue than methods that rely on other detection techniques. Further, in many embodiments, only two fluors are needed for decoding, which provides convenient spectral distinction using simple detection devices and leaves enough spectrum for labeling cellular structure using other fluors. Of course more than two colors can be used to expand the number of sequences that are decoded, using modifications of the method set forth in further detail elsewhere herein and in the references that are incorporated by reference above as describing sequential hybridization of decoder probes to decoder sequences.

The at least first and second decoding sequences can be any suitable length to ensure specific hybridization. Thus, for example, in some embodiments, each decoding sequence can be 3, 4, 5, 6, 7, 8, 9, 10, 11, 12, 13, 14, 15, 16, 17, 18, 19, 20 or greater than 20 nucleotides in length.

In some embodiments, the methods provided herein allow for detection of a single target nucleotide species of interest. In other embodiments, the methods allow for multiplex detection of a plurality of nucleotide species of interest. The use of barcode probes with unique identifier sequences as described above allows for simultaneous detection of 2, 3, 4, 5, 6, 7, 8, 9, 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000 or more than 10,000 unique nucleic acid target molecules within a single cell. Thus, in contrast to existing in situ detection methods, which are limited by the requirement for unique labels (such as fluorescent labels) for each probe type, the methods presented herein have the advantage of virtually limitless numbers of individually detected molecules in parallel and in situ.

Immobilization of Nucleic Acids In Situ

In embodiments presented herein, amplified nucleic acid molecules, barcode probes and other nucleic acid molecules are immobilized within the structure of the cell by crosslinking the nucleic acid to structural proteins in the cell. Any suitable method for immobilizing nucleic acid molecules within a cell may be used in the methods and compositions presented herein.

Detection of Disease-Causing Mutations and/or Common Variants with Specific Padlock Probes The methods and compositions provided herein make it possible to specifically detect one or more disease-causing mutations, alleles or common variants in situ within an individual cell or plurality of cells. Thus in some embodiments, the methods make use of one or more specific barcode probes which are correlated with a disease-causing mutation or mutations, alleles or common variants. In some aspects, the method can comprise ligation of a mutation-specific barcode probe, such as a padlock probe, only when the disease-causing mutation, allele or common variant is present in the nucleic acid molecule.

Any mutation, allele or common variant type can be a target for a mutation-specific barcode probe. The disease-causing mutation, allele or common variant can be, for example, a base substitution, an insertion mutation, a deletion mutation, a gene amplification, a gene deletion, a gene fusion event or gene inversion event or any other mutation which is associated with one or more phenotypes of interest. In some embodiments, the mutation, allele or common variant is associated with an increased predisposition for one or more diseases or other phenotypes. In some embodiments, the mutation, allele or common variant is associated with a decreased predisposition for one or more diseases or other phenotypes. For example, some mutations, alleles or common variants are associated with a cancer phenotype, such as decreased growth inhibition, evasion of immune detection, de-differentiation, and the like. Somatic mutations that can be detected using the method provided herein include for example, mutations to BRAF, EGFR, Her2/ERBB2, and other somatic mutations as exemplified by Greenman et al., Nature (2007) 446:153-158, hereby incorporated by reference in its entirety. Examples of specific barcodes for detection of somatic mutations are provided in the Example section below.

Detection of mutation-specific barcode probes can further comprise evaluating a signal to determine for example, the presence, quantity, frequency, and/or spatial distribution of a disease-causing mutation, allele or common variant within a tissue.

Probes as described herein can also be designed to target specific genomic regions, such as, for example, the specific microsatellite repeat on the X chromosome. In addition, probes can be used as internal controls, either as a positive or negative control, or as a standard for normalization of one or more other signals during detection.

Probes as described herein are also useful for detection of methylation patterns in situ. In such embodiments, nucleic acids within the cell or cells of interest may be subjected to bisulfite conversion as is known in the art. Following bisulfite conversion, one or more methylation-specific barcode probes may be specifically hybridize to a methylation pattern of interest and then amplified for decoding and detection as described above.

Cell Handling for In Situ Detection and Decoding

The methods and compositions make use of hybridization, amplification, washing and detection within individual cells. These methods are performed in situ on isolated cells or in tissue sections that have been prepared according to methodologies known in the art. Methods for permeablization and fixation of cells and tissue samples are well-known in the art, as exemplified by Cremer et al., The Nucleus: Volume 1: Nuclei and Subnuclear Components, R. Hancock (ed.) 2008; and Larsson et al., Nat. Methods (2010) 7:395-397 and associated supplemental materials, the content of each of which is incorporated herein by reference in its entirety. Any suitable permeabilization and/or fixation technologies can be used for making cells and the target nucleic acid molecules therein available for the amplification and detection methods provided herein.

Detection of Signals

The signals generated by fluorescent imaging of one or more probes during decoding, sequencing and other detection methods carried out in situ and can be detected using any suitable imaging and detection technologies which allow for detection of individual amplicons in situ. Suitable imaging technologies are known in the art, as exemplified by Larsson et al., Nat. Methods (2010) 7:395-397 and associated supplemental materials, the entire content of which is incorporated by reference herein in its entirety.

An example demonstrating in situ imaging and 3D reconstruction of in situ detection is set forth in FIG. 1 and Example 1.

Sequencing to Identify Barcode Probe

In some embodiments, the barcode sequence in the barcode probe may be detected and/or decoded in situ by sequencing methodologies, such as direct sequencing, including sequencing by synthesis, sequencing by hybridization, and the like.

One example is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different sites within an individual cell as set forth herein can be subjected to an SBS technique under conditions where events occurring for different templates can be distinguished due to their location within the individual cell.

Flow cells provide a convenient format for housing an individual cell (or a spatially arrayed collection of individually resolvable cells) having amplified nucleic acid molecules produced by the methods of the present disclosure. One or more individual cells in such a format can be subjected to an SBS or other detection technique that involves repeated delivery of reagents in cycles. For example, to initiate a first SBS cycle, one or more labeled nucleotides, DNA polymerase, etc., can be flowed into/through a flow cell that houses one or more individual cells having amplified nucleic acid templates. Those sites of an individual cell where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced in situ by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced in situ according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons in situ that are used to detect protons.

Exemplary methods for array-based expression and genotyping analysis that can be applied to in situ detection according to the present disclosure are described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

An advantage of the methods set forth herein is that they provide for rapid and efficient detection of a plurality of target nucleic acid in parallel. Accordingly the present disclosure provides integrated systems capable of preparing and detecting nucleic acids in situ using techniques known in the art such as those exemplified above. Thus, an integrated system of the present disclosure can include fluidic components capable of delivering amplification reagents to one or more individual cells, the system comprising components such as pumps, valves, reservoirs, fluidic lines and the like. A particularly useful fluidic component is a flow cell. A flow cell can be configured and/or used in an integrated system for in situ detection of target nucleic acids. Exemplary flow cells are described, for example, in US 2010/0111768 A1 and U.S. Ser. No. 13/273,666 (now U.S. Pat. No. 8,951,781), each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq platform (Illumina, Inc., San Diego, Calif.) and devices described in U.S. Ser. No. 13/273,666 (now U.S. Pat. No. 8,951,781), which is incorporated herein by reference.

A system capable of carrying out a method set forth herein need not be integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating a set of amplicons in situ. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

Example 1

Design and Optimization of a Set of Padlock Probes and Hybridization Oligos for Targeted Detection and Quantification of a Subset of Genes This example presents an innovative method based on padlock circularization and hybridization-based decoding (FIG. 1). This method is built upon ultra-high degree multiplexed capture (>300,000 per reaction) using padlock probes for useful for genomic, transcriptomic and methylomic analyses, as well as technology for accurate decoding of randomly assembled bead arrays.

In some embodiments, rolonies for an entire transcriptome can be generated using either random hexamers or oligo-dT primers (FIG. 1A). In some embodiments, rolonies for a specific subset of genes of interest can then be tagged with gene-specific barcodes using a library of padlock probes (FIG. 1B).

Padlock probes are designed in a similar manner as the full transcriptome probe sets previously developed for digital RNA allelotyping according to the incorporated materials disclosed in Zhang, K. et al. Nat Methods 6, 613-618 (2009) and Noggle, S. et al. Nature 478, 70-75 (2011). A neural network, trained for predicting probe efficiency using experimental data accumulated on over 400,000 probes, is integrated into a probe design algorithm called ppDesigner. The entire probe design, synthesis and production process has been highly optimized.

Long oligonucleotides (up to 300 nt in length) acquired from Agilent Technologies contain amplification adaptors to allow production of essentially an unlimited amount of functional padlock probes from a set of seed oligos. The design of the barcoding region incorporates the error-checking scheme described in the incorporated materials of Gunderson et al. (Genome Res. (2004) 14:870-877). For up to 1700 target genes, eight rounds of hybridization decoding are performed. In each round, a rolony can have three states: two fluorescent (FAM and Cy3) "ON" states and one non-fluorescent OFF state. In this three-state, eight-stage decoding scheme, the valid barcode for each gene is required to have exactly two OFF stages and six ON stages for error checking Each padlock probe only needs six slots for hybridization (corresponding to the six ON stages). For the hybridization sequences used in these six slots, a set of 16 (8 stages×2 ON states) 20-mers is selected that are orthogonal to the human genome and have uniform annealing parameters. This eight-stage barcoding scheme is sufficient to decode up to 1792 transcripts with a low error rate ($<10^{-4}$).

Example 2

Design and Optimization of a Set of Padlock Probes for Targeted Detection and Quantification of BRAF V600E, EGFR T790M and EGFR L858R Mutations In this example, allele-specific (padlock) probes are generated for disease causing mutations. Specifically, point mutations are detected in genomic DNA and the decoding scheme is utilized to measure the frequency and spatial distribution of these mutations within tissue sections at single cell resolution. For each of the specifically targeted mutations described below, a padlock probe is designed for specific hybridization to either the wild-type or mutant version of the gene. Then, the padlock probe serves as a template for RCA as described in greater detail herein. The resulting amplicon is detected and decoded using a barcode sequence integrated into the padlock probe.

In an alternative embodiment, the first padlock probe does not comprise a barcode sequence, and a second set of padlock probes is hybridized to the amplicons, and decoder sequences found in the second set of padlock probes are decoded through sequential hybridization as described above.

Probe for Detection of BRAF V600E Mutation

```
(SEQ ID NO: 1) 5'-AACTGATGGGACCCACTCCATCG    [A/T]CTGTAGCTAGACCAAAATCACCTA-3'(SEQ ID NO: 2)
5':CCAGACAACTGTTCAAACTGATGGGACCCACTCCATCGAGATTTC[A/T]CTGTAGCTAGACCAAAATCACCTATTTTACTGTGAGGTCTTCATG-3:
(SEQ ID NO: 3)

Wild-type probe (10101):
CGATGGAGTGGGTCCCATCAGTTATGTATCGCGCTCGATTGGCAGTAGAACTTGCGCGGATACACGGTCGAGGTCCGACTCGGAATACGTCGTTGACTGCG
TAGGTGATTTTGGTCTAGCTACAGT (SEQ ID NO: 4)

Mutant probe (20202):
CGATGGAGTGGGTCCCATCAGTTACGTATCGGTAGTCGCAACGCATCTACTTCGTCGCGTCAGACCATCGAGGTCCGACCTACCATTCGCGTGCGATTCCA
TAGGTGATTTTGGTCTAGCTACAGA (SEQ ID NO: 5)
```

Probe for Detection of EGFR T790M Mutation

```
              (SEQ ID NO: 6) CCACCGTGCAGCTCATCA[C/T]     CATGCCCTTCGGCTGCCTCCT)SEQ ID NO: 7)
TGCCGCCTGCTGGGCATCTGCCTCACCTCCACCGTGCAGCTCATCA[C/T]GCAGCTCATGCCCTTCGGCTGCCTCCTGGACTATGTCCGGGAACA(SEQ ID
NO: 8)
Wild-type probe: 01011
CATGCCCTTCGGCTGCCTCCTGTCTTGCGTGCGATACGGAGTACGAATTGTCCGCGCTCTACGATTCGAGGTCCGACTCGGAATACGTCGTTGACTGCGCCACC
GTGCAG
CTCATCAC (SEQ ID NO: 9)
Mutant Probe: 02022
CATGCCCTTCGGCTGCCTCCTCAACGGTATTCGGTCGTCATCCCCGTTTGATCGTTCGACCGAGATCGAGGTCCGACCTACCATTCGCGTGCGATTCCACCACC
GTGCAG
CTCATCAT SEQ ID NO: 10)
```

Probe for Detection of EGFR L858M Mutation

```
            (SEQ ID NO: 11) GTCAAGATCCAGATTTTGGGC[T/G]    CTGCTGGGTGCGGAAGAGAAAGAATA(SEQ ID NO: 12)
GTACTGGTGAAAACACCGCAGCATGTCAAGATCACAGATTTTGGGC[T/G]GGCCAAACTGCTGGGTGCGGAAGAGAAAGAATACCATGCAGAAGG
(SEQ ID NO: 13)

Wild-type probe: 01012
CTGCTGGGTGCGGAAGAGAAAGAATATAGAACTTGCGCGGATACACGGCGAATTGTCCGCGCTCTACGATTCGAGGTCCGACCTACCATTCGCGTGCGATTCCA
GTCAAGATCCAGATTTTGGGCT (SEQ ID NO: 14)

Mutant Probe:   02201
CTGCTGGGTGCGGAAGAGAAAGAATACAACGGTATTCGGTCGTCATCCTCTACTTCGTCGCGTCAGACCATCGAGGTCCGACTCGGAATACGTCGTTGACTGCG
GTCAAGATCACAGATTTTGGGCG (SEQ ID NO: 15)
```

Example 3

Design and Optimization of a Set of Padlock Probes for Targeted Detection and Quantification of Her2/ERBB2 Amplification and/or Deletion In this example, allele-specific (padlock) probes are generated for Her2/ERBB2 mutations. Specifically, gene amplification and/or deletion is detected in genomic DNA and the decoding scheme is utilized to measure the frequency and spatial distribution of gene amplifications and/or deletions within tissue sections at single cell resolution.

Design, hybridization and detection are performed as described above in Example 2. A specifically designed padlock probe is described below.

Probe for Detection of Her2/ERBB2

(SEQ ID NO: 16) AGCTCTTTGAGGACAACTATGCGCTG      AGACAATGGAGACCCGCTGAAC(SEQ ID NO: 17)
TGTGCGAGGCACCCAGCTCTTTGAGGACAACTATGCGCTGGCCGTGCTAGACAATGGAGACCCGCTGAACAATACCACCCCTGTCACAGGGGCCTCCCCA
(SEQ ID NO: 18)

Wild-Type probe: 20022
AGACAATGGAGACCCGCTGAACACGTATCGGTAGTCGCAACGCACCGTTTGATCGTTCGACCGAGATCGAGGTCCGACCTACCATTCGCGTGCGATTCCAAG
CTCTTTGAGGACAACTATGCGCTG (SEQ ID NO: 19)

Probe for Detection of DXZ4 (chrX Microsatellite Repeat)

(SEQ ID NO: 20) CCTGCTCTCTCTGTCTCAAC      GTGCTGCCCAGGACTTCTTGCC (SEQ ID NO: 21)
CTACTGGGGCCCACTTCCTCTCCTGCTCTCTCTGTCTCAACGTGATTGACTTCTTGTGCTGCCCAGGACTTCTTGCCCACGTGCGCCTTCAAAACGGTAAGAGCT
GCAACTGAACGTG (SEQ ID NO: 22)
Wild-type probe: 11010
                    ATGTATCGCGCTCGATTGGCAGTAGAACTTGCGCGGATACACGG (SEQ ID NO: 23)
GTGCTGCCCAGGACTTCTTGCCATGTATCGCGCTCGATTGGCAGGTCTTGCGTGCGATACGGAGTATCGAGGTCCGACCGAATTGTCCGCGCTCTACGATCCTGCT
CTCTCTGTCTCAAC (SEQ ID NO: 24)

Example 4

Design and Optimization of a Set of Padlock Probes for Targeted Detection and Quantification of Microsatellite Repeat In this example, allele-specific (padlock) probes are generated for detection of chrX microsatellite repeats. Specifically, the specific microsatellite repeats are detected in genomic DNA and the decoding scheme is utilized to evaluate microsatellite repeats within tissue sections at single cell resolution.

Design, hybridization and detection are performed as described above in Example 2. A specifically designed padlock probe is described below.

Probe for Detection of DXZ4 (chrX Microsatellite Repeat)

```
                    CCTGCTCTCTCTGTCTCAAC
CTACTGGGGCCCACTTCCTCTCCTGCTCTCTCTGTCTCAACGTGATTGAC

GTGCTGCCCAGGACTTCTTGCC
TTCTTGTGCTGCCCAGGACTTCTTGCCCACGTGCGCCTTCAAAACGGTA

AGAGCTGCAACTGAACGTG
```

-continued

Wild-type probe: 11010
                    ATGTATCGCGCTCGATTGGCAGTAGAACT
GTGCTGCCCAGGACTTCTTGCCATGTATCGCGCTCGATTGGCAGGTCTTGC

TGCGCGGATACACGG
GTGCGATACGGAGTATCGAGGTCCGACCGAATTGTCCGCGCTCTACGATCC

TGCTCTCTCTGTCTCAAC

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of providing sequence information regarding at least one target nucleic acid sequence in a plurality of nucleic acid molecules from an individual cell comprising:

(a) amplifying a plurality of nucleic acid molecules in situ within a cell, thereby generating a set of amplified nucleic acid molecules, wherein the set of amplified nucleic acid molecules comprise the at least one target nucleic acid sequence;

(b) for each amplified nucleic acid sequence of said set of amplified nucleic acid molecules, annealing in situ a padlock probe that is designed to anneal to the at least one target nucleic acid sequence, wherein the padlock probe comprises two sequence-specific capturing arms on the 5' and 3' end of the probe, wherein the capturing arms are ligatable when each are annealed to the target nucleic acid sequence, wherein the padlock probe further comprises at least a first decoder sequence and a second decoder sequence that do not anneal to said amplified nucleic acid molecules, and wherein the padlock probe can be identified based upon generating a code from decoding the at least first decoder sequence and the second decoder sequence by using sequential hybridization with fluorescently labeled decoder probes, and identifying the padlock probe by matching said code with a reference code that is assigned for each padlock probe, wherein each padlock probe that hybridizes to a different target nucleic acid sequence has a different reference code;

(c) hybridizing a first fluorescently labeled decoder probe to said first decoder sequence, wherein the first fluorescently labeled decoder probe that is not hybridized to said first decoder sequence is removed by washing;

(d) detecting a plurality of fluorescent signals indicative of said hybridizing of the first fluorescently labeled decoder probe to said first decoder sequence;

(e) de-hybridizing and removing the first fluorescently labeled decoder probe;

(f) hybridizing a second fluorescently labeled decoder probe to said second decoder sequence, wherein the second fluorescently labeled decoder probe that is not hybridized to said second decoder sequence is removed by washing, and wherein the second fluorescently labeled decoder probe is labeled with a fluor that absorbs light at a different wavelength than the fluor of the first fluorescently labeled decoder probe;

(g) detecting a plurality of fluorescent signals indicative of said hybridizing of the second fluorescently labeled decoder probe to said second decoder sequence, and (h) determining the identity of the padlock probe based upon decoding the plurality of fluorescent signals generated from hybridization of the first fluorescently labeled decoder probe with the first decoder sequence of the padlock probe, and the plurality of fluorescent signals generated from hybridization of the second fluorescently labeled decoder probe to the second decoder sequence of the padlock probe, wherein identification of the padlock probe provides sequence information regarding the at least one target nucleic acid sequence in the plurality of nucleic acid molecules from an individual cell.

2. The method of claim 1, wherein said amplifying a plurality of nucleic acid molecules in situ within a cell comprises rolling circle amplification.

3. The method of claim 1, wherein said amplified nucleic acid molecules are immobilized within said cell.

4. The method of claim 1, wherein said amplified nucleic acid molecules are amplified from cellular RNA.

5. The method of claim 4, further comprising cDNA synthesis using said cellular RNA.

6. The method of claim 1, wherein said amplified nucleic acid molecules comprise DNA.

7. The method of claim 1, wherein said nucleic acid molecules comprise a disease-causing mutation.

8. The method of claim 7, wherein said disease-causing mutation comprises a base substitution.

* * * * *